US005458597A

United States Patent [19]

Edwards et al.

[11] Patent Number: 5,458,597
[45] Date of Patent: Oct. 17, 1995

[54] DEVICE FOR TREATING CANCER AND NON-MALIGNANT TUMORS AND METHODS

[75] Inventors: Stuart D. Edwards, Los Altos; Ronald G. Lax, Grass Valley; Hugh R. Sharkey, Redwood Shores, all of Calif.

[73] Assignee: ZoMed International, Menlo Park, Calif.

[21] Appl. No.: 148,439

[22] Filed: Nov. 8, 1993

[51] Int. Cl.$^6$ ..................................................... A61B 17/39
[52] U.S. Cl. .................. 606/41; 606/49; 606/50; 604/21
[58] Field of Search ..................... 606/27–31, 41, 606/45–50; 607/96, 98–102, 115, 116, 120, 154; 604/22, 21; 128/642

[56] References Cited

U.S. PATENT DOCUMENTS

| | | |
|---|---|---|
| 3,474,777 | 10/1969 | Figge et al. . |
| 3,987,795 | 10/1976 | Morrison . |
| 4,033,351 | 7/1977 | Hetzel . |
| 4,043,342 | 8/1977 | Morrison, Jr. . |
| 4,269,174 | 5/1981 | Adair ......................................... 606/29 |
| 4,303,636 | 12/1981 | Gordon . |
| 4,331,654 | 5/1982 | Morris . |
| 4,337,760 | 7/1982 | Rubin ......................................... 604/52 |
| 4,345,588 | 8/1982 | Widder et al. . |
| 4,506,680 | 3/1985 | Stokes . |
| 4,524,770 | 6/1985 | Orandi ........................................ 606/46 |
| 4,532,924 | 8/1985 | Auth et al. . |
| 4,545,368 | 10/1985 | Rand et al. . |
| 4,562,838 | 1/1986 | Walker . |
| 4,565,200 | 1/1986 | Cosman .................................... 606/50 |
| 4,574,782 | 3/1986 | Borrelli et al. . |
| 4,586,490 | 5/1986 | Katz . |
| 4,652,257 | 3/1987 | Chang . |
| 4,662,359 | 5/1987 | Gordon . |
| 4,690,130 | 9/1987 | Mirell . |
| 4,692,139 | 9/1987 | Stiles . |
| 4,753,248 | 6/1988 | Engler et al. . |
| 4,763,671 | 10/1988 | Goffinet . |
| 4,776,086 | 10/1988 | Kasevich et al. . |
| 4,800,899 | 1/1989 | Elliott . |
| 4,813,429 | 3/1989 | Eshel et al. . |
| 4,818,542 | 4/1989 | DeLuca et al. . |
| 4,823,793 | 4/1989 | Angulo et al. . |
| 4,860,744 | 8/1989 | Johnson et al. . |

(List continued on next page.)

FOREIGN PATENT DOCUMENTS

2-121675  5/1990  Japan .

*Primary Examiner*—Stephen C. Pellegrino
*Assistant Examiner*—Michael Peffley
*Attorney, Agent, or Firm*—Haynes & Davis

[57] ABSTRACT

A method of this invention for treating body tissues containing cancerous cells or non-malignant tumors with RF ablation, alone or in combination with systemic or localized chemotherapy comprising introducing a stylet comprising an electrode surface and a sleeve longitudinally moveable thereon into the vicinity of the body tissues, retracting the sleeve from a portion of the electrode surface, and supplying RF power to the electrode surface sufficient to heat the tissue to a temperature of above about 45° C. for a time to cause reduction of tissue mass in the vicinity of the electrode. The RF power supplied to the electrode surface is sufficient to effect a desiccated fluid diffusion barrier capsule surrounding the body tissue being treated. The stylet can include a hollow tube having fluid distribution ports therein, and the method can include the step of passing fluid through one or more distribution ports into the body tissue being treated. The fluid can be saline or a chemotherapeutic fluid such as liquid or gas containing a cytotoxic agent, for example. The fluid can be administered in a variety of procedures. The fluid can be passed through a distribution port into the body tissue before, during and/or after the RF power is supplied to the electrode surface, for example. Preferably, the fluid is introduced after a barrier capsule has been formed. The devices comprises electrodes having a hollow core and a closed sharpened distal tip. The electrode has a plurality of fluid distribution ports therein for distribution of fluid treatment agents into the tissue.

19 Claims, 8 Drawing Sheets

U.S. PATENT DOCUMENTS

| | | |
|---|---|---|
| 4,907,589 | 3/1990 | Cosman . |
| 4,920,978 | 5/1990 | Colvin . |
| 4,931,047 | 6/1990 | Broadwin et al. . |
| 4,945,912 | 8/1990 | Langberg . |
| 4,947,842 | 8/1990 | Marchosky et al. . |
| 4,963,364 | 10/1990 | Fox et al. . |
| 4,966,604 | 10/1990 | Reiss . |
| 4,976,680 | 12/1990 | Hayman et al. . |
| 4,976,711 | 12/1990 | Parins et al. . |
| 4,983,159 | 1/1991 | Rand . |
| 4,989,601 | 2/1991 | Marchosky et al. . |
| 5,009,656 | 4/1991 | Reimels . |
| 5,013,312 | 5/1991 | Parins et al. . |
| 5,015,227 | 5/1991 | Broadwin et al. . |
| 5,016,615 | 5/1991 | Driller et al. . |
| 5,026,959 | 6/1991 | Ito et al. . |
| 5,047,027 | 10/1991 | Rydell . |
| 5,055,100 | 10/1991 | Olsen . |
| 5,057,107 | 10/1991 | Parins et al. . |
| 5,059,199 | 10/1991 | Okada et al. . |
| 5,067,952 | 11/1991 | Gudov et al. . |
| 5,071,419 | 12/1991 | Rydell et al. . |
| 5,078,717 | 1/1992 | Parins et al. . |
| 5,080,660 | 1/1992 | Buelna . |
| 5,084,001 | 1/1992 | Van't Hooft et al. . |
| 5,084,045 | 1/1992 | Helenowski . |
| 5,085,659 | 2/1992 | Rydell . |
| 5,100,423 | 3/1992 | Fearnot . |
| 5,119,832 | 6/1992 | Xavier ........................................ 607/120 |
| 5,122,137 | 6/1992 | Lennox ....................................... 606/42 |
| 5,125,928 | 6/1992 | Parins et al. . |
| 5,167,626 | 12/1992 | Casper et al. . |
| 5,169,396 | 12/1992 | Dowlatshahi et al. . |
| 5,170,789 | 12/1992 | Narayan et al. . |
| 5,170,805 | 12/1992 | Kensey et al. . |
| 5,183,455 | 2/1993 | Hayman et al. . |
| 5,190,539 | 3/1993 | Fletcher et al. . |
| 5,190,766 | 3/1993 | Ishihara . |
| 5,197,466 | 3/1993 | Marchosky et al. . |
| 5,197,963 | 3/1993 | Parins . |
| 5,197,964 | 3/1993 | Parins . |
| 5,203,782 | 4/1993 | Gudov et al. . |
| 5,205,289 | 4/1993 | Hardy et al. . |
| 5,207,675 | 5/1993 | Canady . |
| 5,217,458 | 6/1993 | Parins . |
| 5,236,410 | 8/1993 | Granov et al. . |
| 5,236,424 | 8/1993 | Imran . |
| 5,246,438 | 9/1993 | Langberg . |
| 5,277,696 | 1/1994 | Hagen . |
| 5,281,213 | 1/1994 | Milder et al. . |
| 5,281,217 | 1/1994 | Edwards et al. . |
| 5,281,218 | 1/1994 | Imran . |
| 5,286,253 | 2/1994 | Fucci . |
| 5,290,286 | 3/1994 | Parins . |
| 5,295,955 | 3/1994 | Rosen et al. . |
| 5,300,069 | 4/1994 | Hunsberger et al. . |
| 5,300,099 | 4/1994 | Rudie . |

DEVICE FOR TREATING CANCER AND NON-MALIGNANT TUMORS AND METHODS

RELATIONSHIP TO COPENDING APPLICATIONS

This application is related to concurrently filed, copending application Ser. No. 08/148,441, the entire contents of which are hereby incorporated by reference.

1. FIELD OF THE INVENTION

This invention is directed to a novel device and method for treating body tissues which include neoplastic cells, such as cancerous tissue and non-malignant tumors, to reduce the mass thereof. The device penetrates normal tissue to reach the tissue including the neoplasm and delivers therapeutic ablative energy to the tissue and/or deliver therapeutic substances to the tissue. It limits delivery of the therapeutic treatment to the precise location selected. This device is a cannula device for positioning a treatment assembly in the area or organ containing the neoplasm with at least one styler in the cannula, mounted for extension from the end of the cannula through surrounding tissue to the tissue targeted for medical treatment. This device is suitable for reducing the mass of any type of tissue, and it is most particularly useful for treating tissue containing neoplastic cells.

2. BACKGROUND OF THE INVENTION

Surgical treatment of cellular tissues usually requires direct contact of target tissue with a medical instrument, usually exposing both the target and intervening tissue to substantial trauma. Often, precise placement of a treatment probe is difficult because of the location of a target tissue in the body or the proximity of the target tissue to obstructions or easily damaged, critical body organs, nerves, or other components.

High-frequency currents are used in electrocautery procedures for cutting human tissue, especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated. The frequency of the current for this use must be above ca. 300 kHz in order to avoid any adverse such as nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radiofrequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, tissues in organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to kill the tissue constricting the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Chemotherapy generally involves systemic delivery of the therapeutic agents, the agents affecting both normal dividing and abnormal cells. Efforts to target neoplastic cells, such as with "bullets" comprising a neoplastic preferentially binding antibody coupled with a cytotoxic agent have had limited success; the agents are removed and concentrated by the liver in the removal process, exposing the liver to high levels of the toxin. Photodynamic therapy seeks to limit the cytotoxic activity to the areas exposed to light energy; however, since the photodynamic agents are administered systemically, epidermal areas exposed to light are also affected, requiring protection from the sun until the photodynamic agents are eliminated from the body.

OBJECTS AND SUMMARY OF THE INVENTION

It is one object of this invention to provide a device and method for treating body tissues containing neoplastic tissue such as cancerous tissue and non-malignant tumors to reduce the mass thereof.

It is another object of this invention to provide a device for combined therapeutic ablation and chemotherapy which forms an infusion barrier surrounding the tissue to be treated, the barrier substantially confining liquid treatment agents administered by the device to the zone within the capsule of the infusion barrier.

It is a further object of this invention to provide a device for therapeutic ablation and chemotherapy which increases distribution of therapeutic agents through target tissue by use of the ablative heat, alternating with or concurrent with tissue ablation.

It is a still further object of this invention to stimulate reduction of neoplastic cells in an organ or body tissue containing one or more neoplastic sites by applying therapeutic ablative energy to a portion of the organ or body tissue, alone or in combination with the application of chemotherapy.

In summary, the method of this invention for treating body tissues containing cancerous cells or non-malignant tumors comprises a) introducing a styler comprising an electrode surface and a sleeve longitudinally moveable thereon into the vicinity of the body tissues, b) retracting the sleeve from a portion of the electrode surface, and c) supplying RF power to the electrode surface sufficient to heat the tissue to a temperature of above about 45° C. for a time to cause reduction of tissue mass in the vicinity of the electrode. In one embodiment of the method, the RF power supplied to the electrode surface is sufficient to form a desiccated fluid diffusion barrier capsule surrounding the body tissue being treated.

Preferably, the stylet includes a hollow tube having fluid distribution ports therein, the tube comprising a fluid supply means. The method includes the step of passing fluid through distribution ports into the body tissue being treated. The fluid can be saline or a chemotherapeutic fluid such as liquid containing a cytotoxic agent or a cytotoxic gas, for example.

The fluid can be administered in a variety of procedures. The fluid can be passed through the distribution ports into the body tissue before, during and/or after the RF power is supplied to the electrode surface, for example. Preferably, fluid is introduced after a barrier capsule has been formed.

In summary, a medical ablation device of this invention for treating tissues containing cancerous cells and for treating non-malignant tumors comprises a tubular RF electrode for reducing mass of the tissues by ablative treatment. The electrode can have a hollow core and a closed, sharpened distal tip, the electrode being enclosed in an insulating sleeve which is optionally longitudinally moveable thereon. The electrode can have a plurality of fluid distribution ports therein for distribution of fluid treatment agents into the tissue. Optionally, the device can include a tube within the electrode and axially concentric therewith, the tube being axially moveable in the electrode to block or close selected fluid distribution ports and prevent fluid passage therethrough.

One embodiment of this invention is a medical ablation device with an electrode, the electrode comprising a support tube. The outer surface of the support tube can support a plurality of conductive and electrically isolated sleeve segments adjacent to one another, each conductive sleeve segment being connected to a source of RF power. Each sleeve segment can be separated from and insulated from an adjacent sleeve segment 14 by an annular insulator, the space between each annular insulator and an adjacent sleeve comprising a gas distribution outlet. The support can have fluid distribution ports, each fluid distribution port being positioned under an annular insulator, whereby fluid passing through each fluid distribution port passes outward through a gas distribution outlet. Optionally, the device can include an outer sleeve means extending over the conductive sleeves and annular insulators, the outer sleeve being longitudinally moveable thereon for blocking selected gas distribution outlets.

DETAILED DESCRIPTION OF THE INVENTION

The medical ablation devices of this invention are uniquely superior for localized therapeutic ablation to remove or reduce undesired tissue masses from remote locations in the body. With a suitably shaped rigid or flexible delivery tubes, the devices can be used with conventional delivery systems including scopes such laparoscopes, cystoscopes, and the like. With delivery tubes such a needles, the device with a memory shaped electrode can be used to ablated undesired tissue in orthopedic, neurological, gynecological and for less invasive surgical applications such as near zero surgical ablation of spinal discs to alleviate encroachment and pressure from herniated disks on adjacent nerves in the spinal column.

Figure 1:
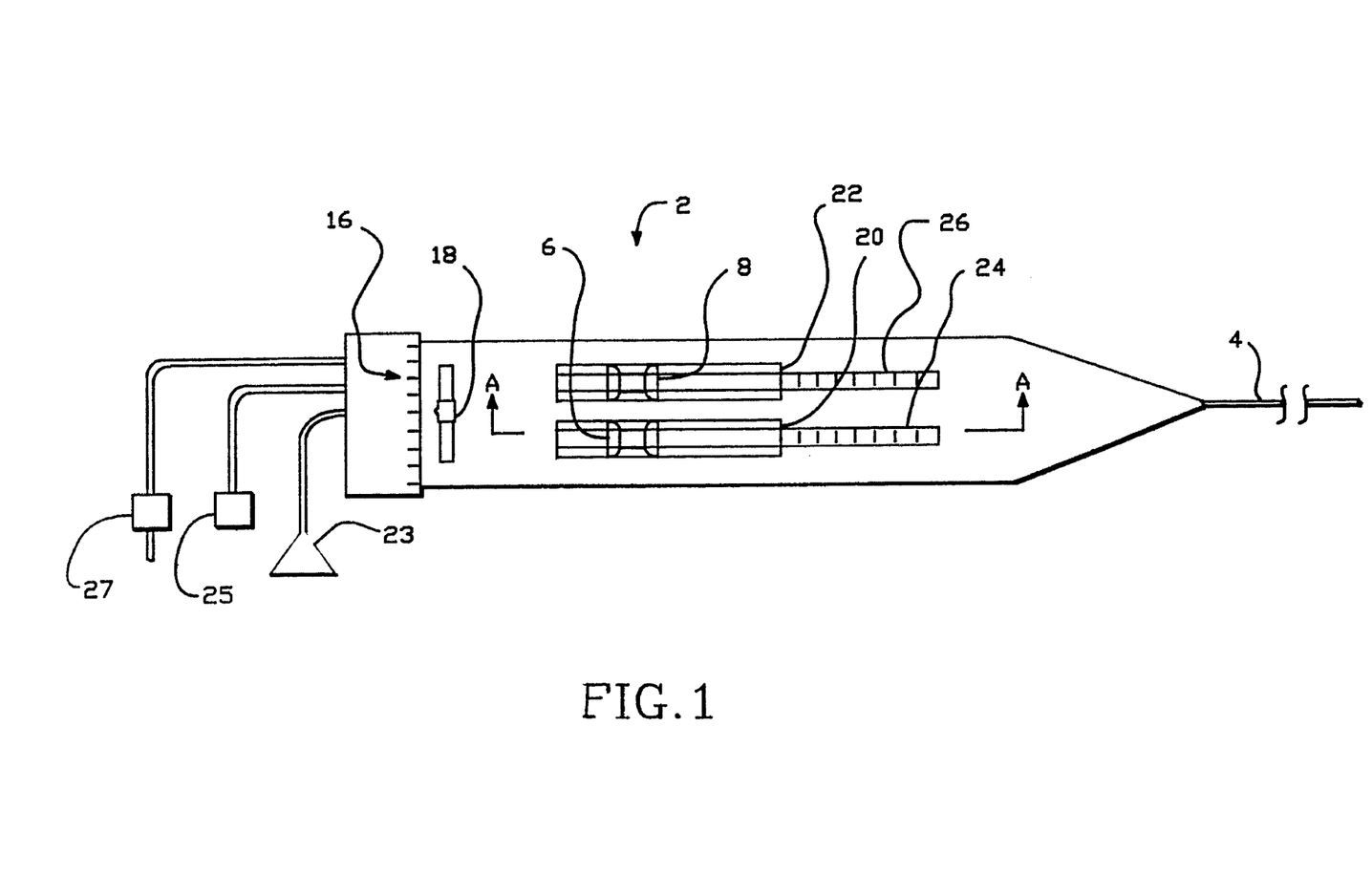
FIG. 1 is a planar view of a stylet ablation device of this invention.
Figure 2:
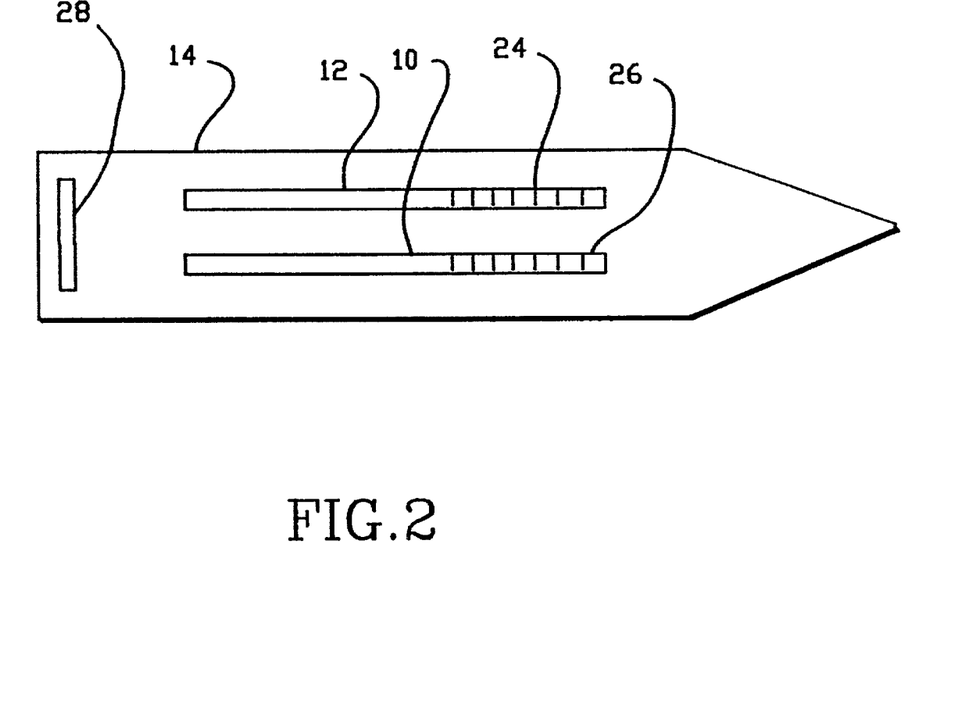
FIG. 2 is a top view of the handle top plate of the stylet ablation device shown in FIG. 1.

Referring to the drawings, FIG. 1 is a planar view of a stylet ablation device of this invention. The device comprises a handle portion 2 and a delivery tube portion 4. Stylet sleeve control manual tab 6 and stylet electrode control manual tab 8 are mounted for sliding engagement in slots 10 and 12 in the handle top plate 14 (FIG. 2). Index markings 16 indicate the relative angle of orientation of the stylet with respect to the stylet angle indicator 18. Angle indicator 18 can be a bubble in a curved transparent tube, a weighted pivot dial indicator or an electronic angle indicator. The position of the distal edges 20 and 22 of the tab slides 6 and 8 with their respective gauge reference strips 24 and 26 independently indicate the relative advancement and retraction of the stylet electrode and sleeve shown in FIGS. 2–4.

Connectors for the fiber optic connector 23, RF power connector 25, and ohmic resistance detector 27 extend from the proximal end of the handle housing.

FIG. 2 is a top view of the handle top plate of the stylet ablation device shown in FIG. 2. Slots 10 and 12 receive respective tabs 6 and 8 for sliding engagement therein. Slot 28 receives the stylet angle indicator.

Figure 3:
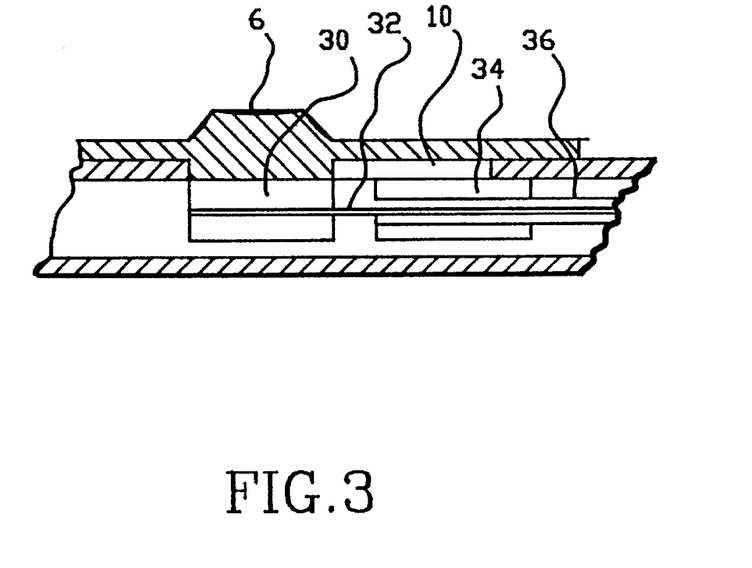
FIG. 3 is a fragmentary cross-sectional view of the manual control portion of the handle of the stylet ablation device shown in FIG. 1, taken along the line A—A in FIG. 1.

FIG. 3 is a fragmentary cross-sectional view of the manual control portion of the handle of the stylet ablation device shown in FIG. 1, taken along the line A—A. Manual electrode tab 6 is attached to an electrode connector 30 which is connected to the proximal end of the stylet electrode 32. Manual sleeve tab 8 (FIG. 1) is connected to a sleeve connector 34 which is connected to the proximal end of the sleeve 36.

The electrode 32 is preferably made of a flexible, shape memory metal such as nickel-titanium alloy or tempered steel. The sleeve is made of a highly conformable insulating plastic material such as polyimide.

Simultaneous forward and rearward movement of the control tabs 6 and 8 effect simultaneous advancement and retraction of the treatment stylet. Individual movement of the control tabs 6 and 8 provide individual advancing and retracting movement of the respective sleeve and electrode. Indexing strips 24 and 26 provide reference points for controlled positioning of the sleeve control tabs 6 and 8, permitting precise, independent positioning of the stylet elements for controlled ablation of remote body portions as is explained in greater detail hereinafter.

Figure 4:
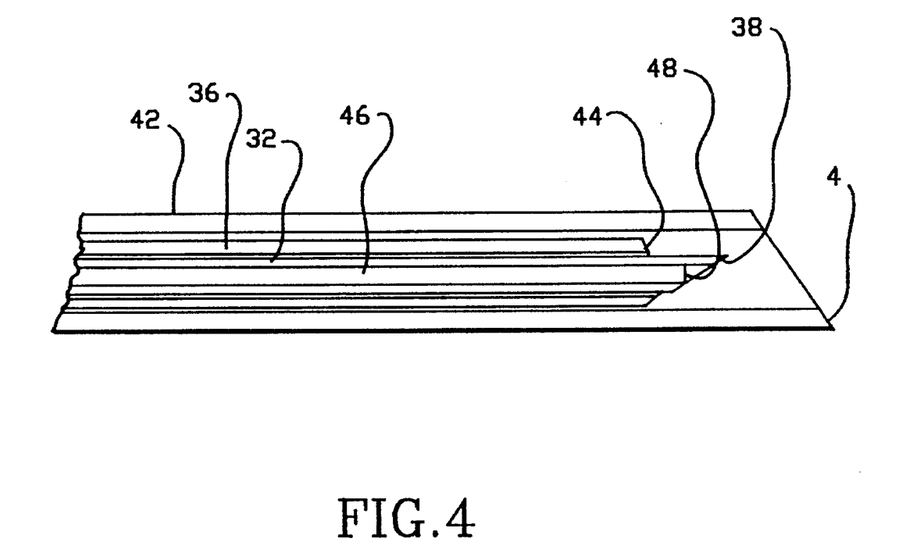
FIG. 4 is a fragmentary cross-sectional view of the tip of the stylet ablation device such as that shown in FIG. 1 with the stylet retracted into the tip.

FIG. 4 is a cross-sectional view of the tip of the stylet ablation device such as that shown in FIG. 1 with the stylet retracted into the tip for initial insertion to a position accessible with a straight needle. The electrode tip 38 is positioned behind the leading sharpened tip 40 of the needle or tube 42. The insulating sleeve tip 44 is positioned just behind the leading edge of the electrode tip 38.

When the electrode 32 is a hollow tube, it can be a conduit for aspiration during treatment, liquid deliver, or in the embodiment shown, a housing for a fiber optic 46. The polished fiber optic tip 48 is then positioned behind the electrode tip 38 to facilitate viewing of the tissue surrounding the electrode tip during insertion.

Figure 5:
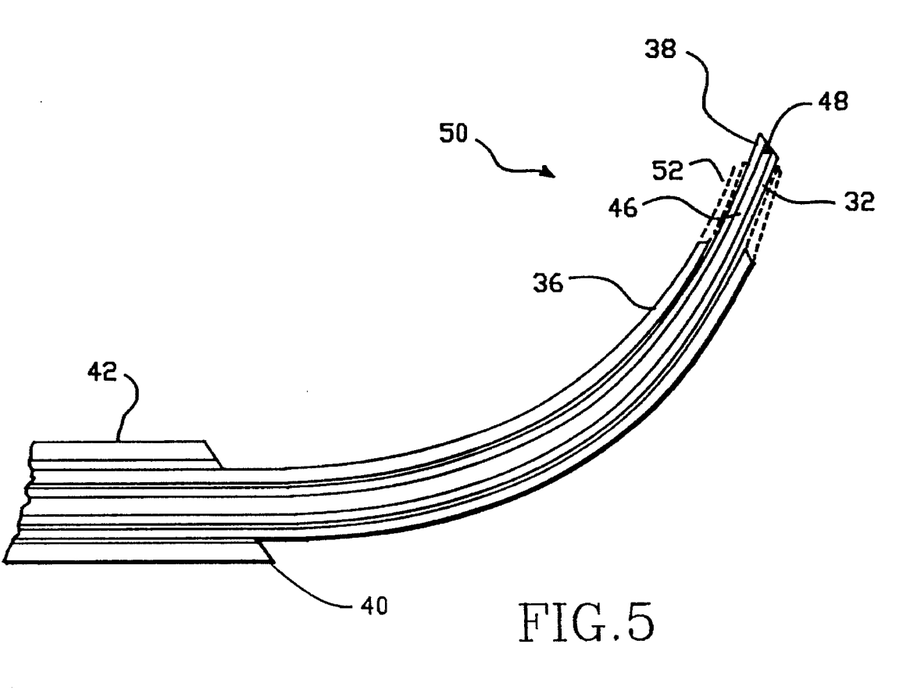
FIG. 5 is a fragmentary cross-sectional view of the tip of the stylet ablation device shown in FIG. 4 with the electrode and sleeve extended from the tip.

FIG. 5 is a cross-sectional view of the tip of the stylet ablation device shown in FIG. 4 with the electrode and sleeve extended. This embodiment shows a flexible stylet 50 having a predetermined curved configuration. The flexible stylet can also be straight, if the remote position can be reached by a straight path from the point of entry without damaging a vital body component. The electrode can be made of a shape memory alloy, shaped to the revert to a desired configuration when released from the tubing. The configuration can be simple curves, a combination of straight portions and curves, curves with differing radii, in two or three dimensions, selected to direct the electrode and its surrounding flexible, highly conformable sleeve in a preselected two or three dimensional path through tissue to a site to be ablated.

Methods for shaping shape memory alloys are well known in the art and are not a part of this invention. In general, the alloys are annealed with heat and then set in the desired memory shape by quick cooling the annealed electrode while maintaining it in the non-linear shape ultimately desired.

The sleeve 36 is initially in the dotted line position 52. Following insertion into the body to the specific site to be ablated, the sleeve 36 is withdrawn from a selected portion of the electrode 32 to the solid line position to expose the specific electrode area required to form a lesion of the desired size.

A method of this invention for medical ablation of difficult to access tissues comprising first inserting a hollow needle through a tissue layer, the needle enclosing a conductive electrode of highly flexible memory metal having a predetermined curved memory configuration and a sharpened distal terminus, the electrode tube being enclosed within an insulating sleeve axially moveable thereon and bendable therewith. Then the electrode and sleeve are advanced from the terminal end of the hollow needle, whereby the portion of the electrode and sleeve advanced beyond the end of the needle adopt the predetermined curved memory configuration and the electrode and sleeve follow a correspondingly predetermined curved path through tissue to the site to be ablated Then a portion of the sleeve is withdrawn from the terminus of the electrode to expose a predetermined electrode area for ablation. Finally, RF energy is applied to the tissue surrounding the exposed electrode area to effect ablation thereof.

Figure 6:
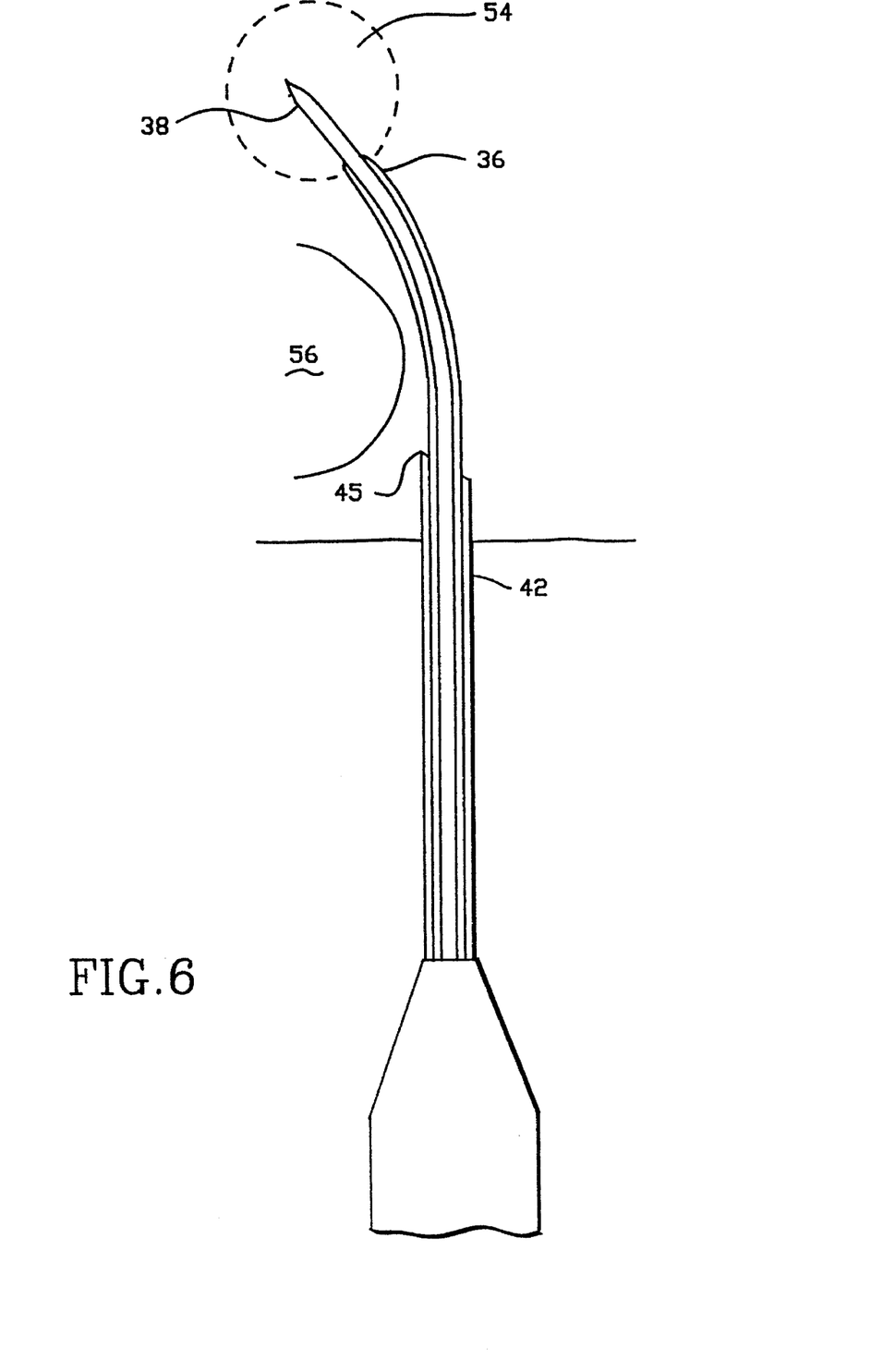
FIG. 6 is a schematic view showing use of an embodiment with a shape memory electrode preformed into a curved shape to ablate a tissue mass behind an obstacle such as a vertebra.

Referring to FIG. 6, use of an embodiment with a shape memory electrode preformed into a curved shape to ablate a near zero access area behind an obstruction in the body. The objective of the treatment is to reduce the size of the mass 54 behind a rigid obstacle such as bone 56 (or area to be protected from penetration). The electrical conductor and sleeve is extended from the needle 40 through surrounding tissue around the obstacle to its back surface, and the target tissue to be reduced. The sleeve 36 is then withdrawn to a position exposing the electrode area required to ablate the tissue mass. Heat is generated in the target tissue from an electric current or electromagnetic field produced by the electrical conductor. Preferably, the volume of tissue being treated is controlled by moving the non-conductive sleeve to expose a selected length of electrode in the body tissue to be treated, the remaining area of the electrode remaining shielded by the sleeve to protect the intervening tissues. The amount and duration of the energy delivery is also varied to control the volume of tissue being treated. The current passes to a large surface area grounding plate contacting the outer skin surface.

Figure 7:
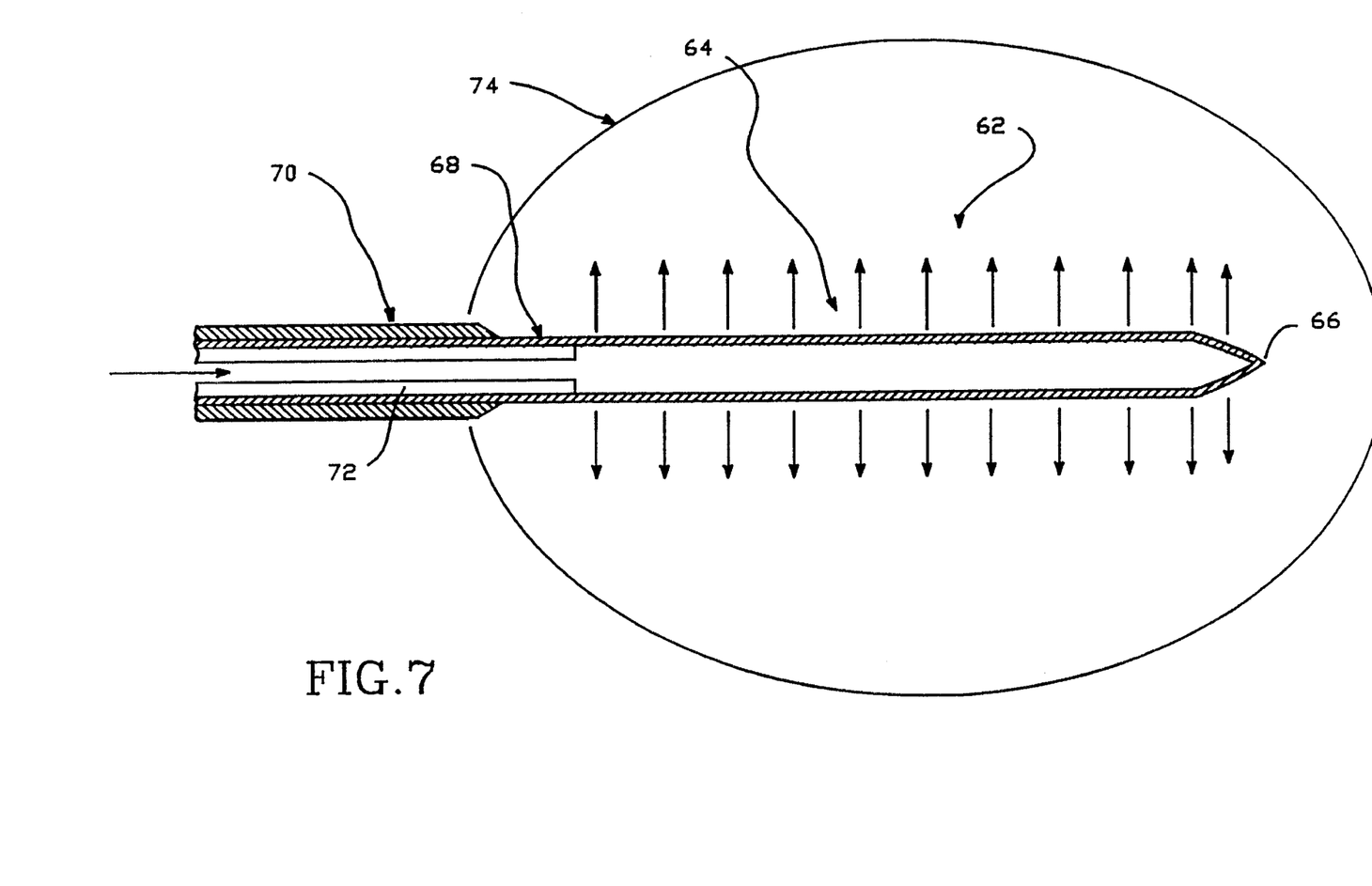
FIG. 7 is a cross-sectional view of a RF stylet including chemotherapy agent distributors.

FIG. 7 is a cross-sectional view of a RF stylet including chemotherapy agent distributors of this invention. In this embodiment, the stylet 60 includes an electrode 62 having the configuration of a tube 64 with a sharp-tipped, closed distal end 66 and a plurality of fluid outlet openings 68, distributed along the length of the exposed electrode portion. The electrode 62 is enclosed within an insulating sleeve 70 which is longitudinally slidable on the electrode, as described above, to control the length and surface of electrode exposed to the surrounding tissue. The tube can optionally contain an inner unperforated tube 72, the position of which can be adjusted to expose a selected number of fluid distribution ports. The treatment fluid flows outwardly through the distribution ports as shown by the arrows extending outwardly therefrom The stylet 60 is advanced to the tissue to be ablated, and the sleeve 70 is withdrawn, exposing a controlled length of electrode and selected number of fluid distribution ports. RF energy is applied, raising the temperature in the lesion site to a temperature of above 45°. For creating an infusion barrier capsule 74, the temperature can be from about 45° C. to 170 ° C. and is preferably from about 80° C. to 120° C. The desiccation boundary 74 acts as a barrier to fluid flow, forming a capsule and restraining escape of fluid introduced through the ports.

In one embodiment of the method of this invention, the infusion boundary is created before fluid is introduced, to restrain its escape from beyond the ablation zone. In another embodiment, the fluid introduction precedes or is concurrent with the application of RF energy, whereby the heating facilitates and increases the penetration of the tissue by the chemotherapeutic fluid. It will be readily apparent to a person skilled in the art that other variations and sequences, and repetitions thereof, can be applied within the scope of this invention to control the zone of treatment and fluid delivery according to the physician's desired objective.

Figure 8A:
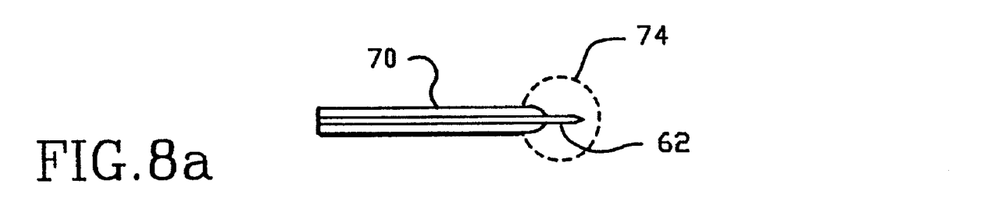
FIGS. 8a, 8b and 8c are schematic views of tissue undergoing capsular ablation according to this invention, demonstrating sleeve adjustments of the device of FIG. 7 to effect a desired ablation lesion geometry.
Figure 8B:
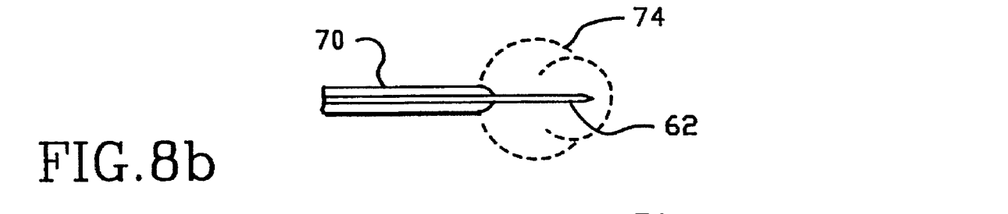
Figure 8C:
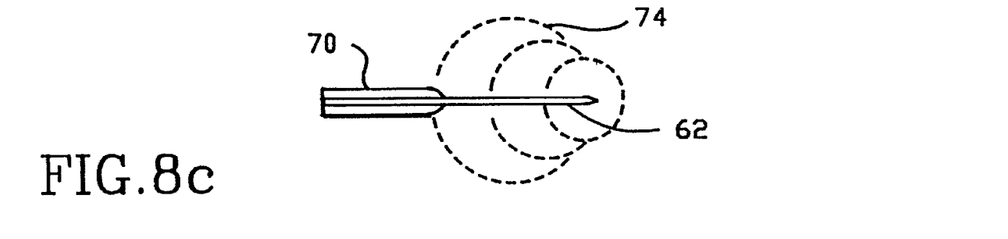

FIGS. 8a, 8b and 8c are schematic views of tissue undergoing capsular ablation according to this invention, demonstrating sleeve adjustments of the device of FIG. 7 to effect a desired ablation lesion geometry. FIG. 8a shows an initial lesion formed with a short portion of electrode 62 extending beyond the insulating sleeve 70. In FIG. 8b, the sleeve 70 has been retracted to expose a longer portion of electrode 62, producing a lesion with a larger radius, pronounced in the portion which beyond the infusion barrier formed in the ablation of FIG. 8a. In FIG. 8c, the sleeve 70 has been retracted to expose a still longer portion of electrode 62, producing a lesion with a still larger radius, pronounced in the portion which beyond the infusion barriers formed in the ablations of FIGS. 8a and 8b. The ultimate lesion barrier has an approximately, overall conical configuration.

Figure 9A:
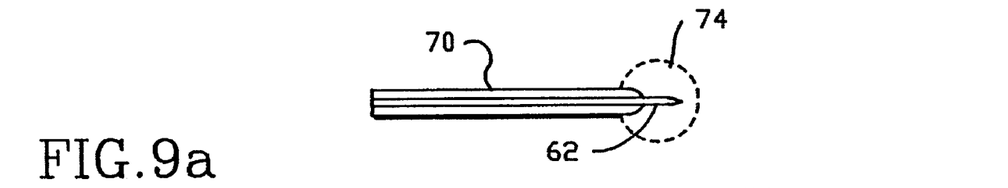
FIGS. 9a, 9b, 9c and 9d are schematic views of tissue undergoing capsular ablation according to this invention, demonstrating stylet position adjustment of the device of FIG. 7 to effect a desired ablation lesion geometry.
Figure 9B:
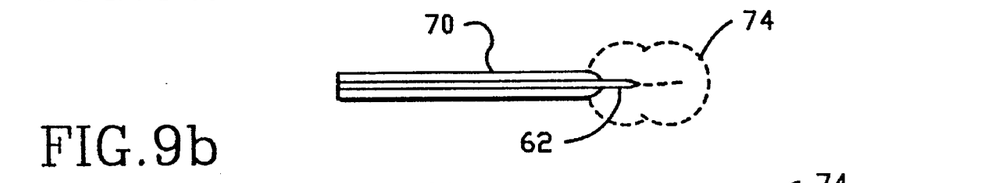
Figure 9C:
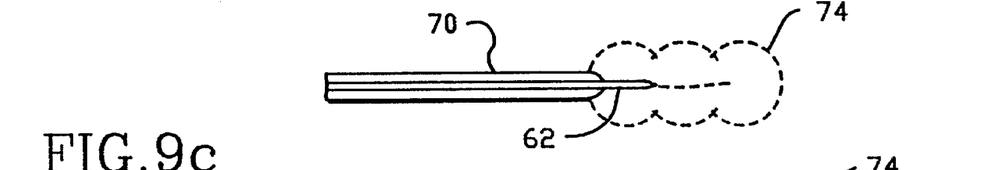
Figure 9D:
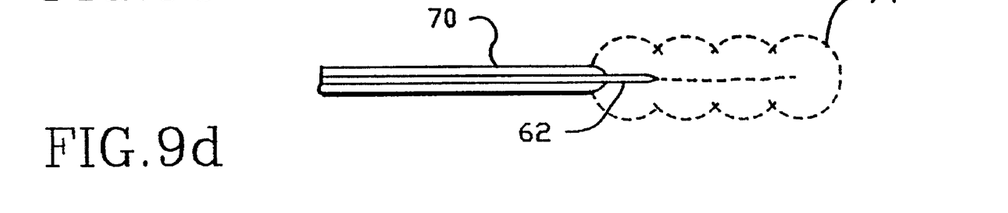

FIGS. 9a, 9b, 9c and 9d are schematic views of tissue undergoing capsular ablation according to this invention, demonstrating stylet position adjustment of the device of FIG. 7 to effect a desired ablation lesion geometry. FIG. 9a shows an initial ablation lesion formed with the stylet extending to a maximally distal position and with a small portion of the electrode 62 extended beyond the insulating sleeve 70. FIGS. 9b, 9c and 9c show successive positions and overlapping lesions formed by incrementally retracting the stylet in the proximal position, performing an ablation at each incremental position to provide an ultimate lesion barrier having an approximately, overall cylindrical configuration.

It will be readily apparent to a person skilled in the art that other sequences, including combinations of sequences illustrated in FIGS. 8a, 8b and 8c, and in FIGS. 9a, 9b and 9c can be devices without departing from the spirit and scope of this invention, and all of these combinations and variations are considered to be within the scope of this invention.

Figure 10:
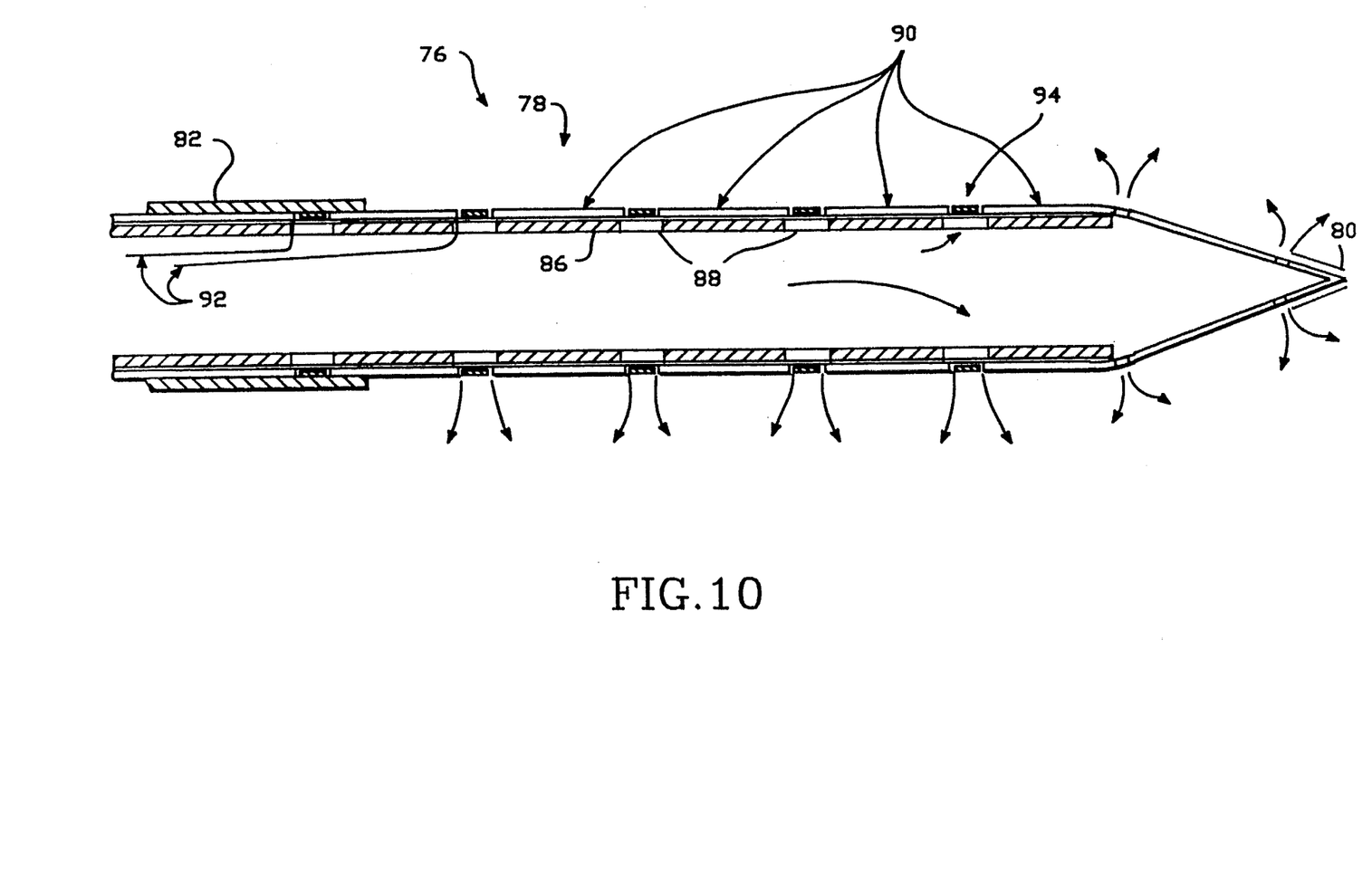
FIG. 10 is a cross-sectional view of an alternate embodiment of a RF stylet including chemotherapy agent distributors and a plurality of annular electrode conductors.

FIG. 10 is a cross-sectional view of an alternate embodiment of a RF stylet including chemotherapy agent distributors and a plurality of annular electrode conductors. In this embodiment, the stylet 76 comprises an electrode and distribution outlet bearing section 78 with a closed sharpened tip 80 and an insulating sleeve 82 longitudinally moveable thereon. The electrode section comprises an inner support tube 86 with fluid distribution ports 88 spaced along its length. Between each pair of ports 88 are positioned conductive sleeve segments or annular coatings 90. Each conductive sleeve segment 90 is connected to an individual insulated electrical RF power lead 92 connected to a switching and power delivery console (not shown). Suitable power supplies are described in copending application Ser. No. 08/061,072 filed May 14, 1993, the entire contents of which are hereby incorporated by reference. Between each conductive sleeve segment 90 is positioned an annular insulating sleeve or ring 94. Fluid passing outwardly through the ports 88 pass between the conductive sleeves segments 90 and the insulating rings 94 to pass outward into the surrounding tissue as shown by the arrows extending outwardly from the spaces between the sleeve segments 90 and rings 94.

Figure 11:
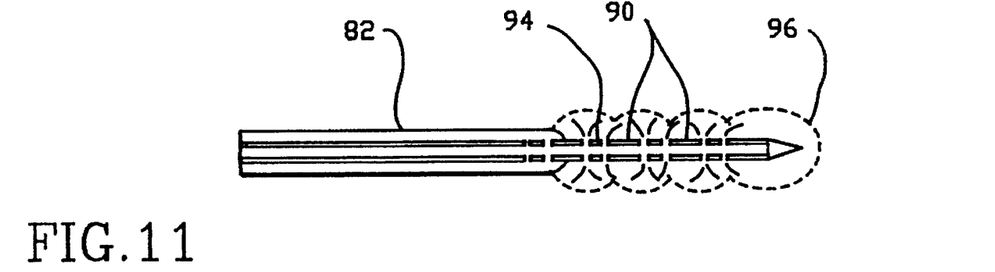
FIG. 11 is a schematic view of tissue undergoing capsular ablation according to this invention, demonstrating a monopolar ablation with a plurality of electrodes with the embodiment shown in FIG. 10 to provide an approximately cylindrical ablation barrier capsule.

FIG. 11 is a schematic view of tissue undergoing capsular ablation according to this invention, demonstrating a monopolar ablation with a plurality of electrodes with the embodiment shown in FIG. 10 to provide an approximately cylindrical ablation barrier capsule. In this embodiment, the power leads are delivering power to each conductive sleeve 90, causing current to pass outwardly from each sleeve through the surrounding tissue. This forms a roughly spherical, overlapping ablation barrier 96 around each conductive sleeve, producing a roughly cylindrical ablation barrier capsule within which the optional treatment fluids are restrained or contained.

Figure 12:
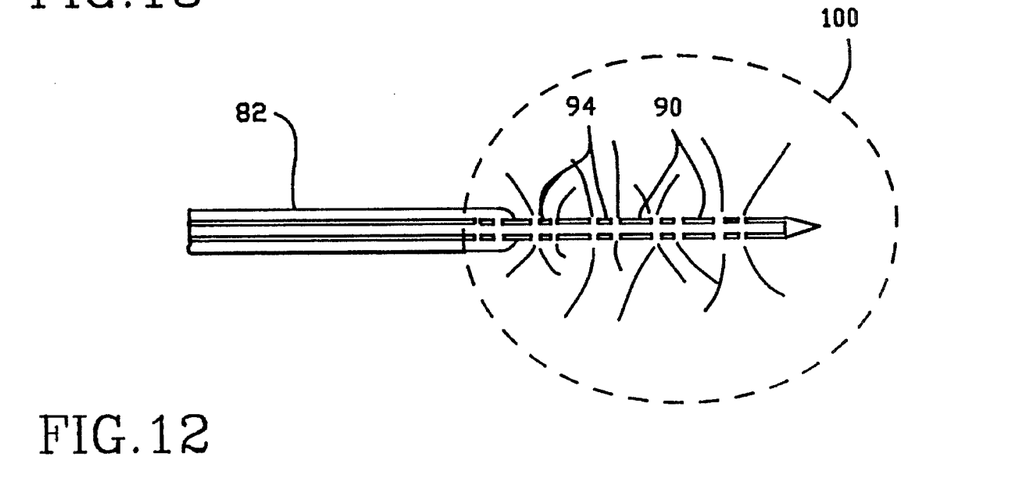
FIG. 12 is a schematic view of tissue undergoing capsular ablation according to this invention, demonstrating extended monopolar mode applications with the embodiment shown in FIG. 10 to effect an encapsulated combined ablation and chemotherapy lesion.

FIG. 12 is a schematic view of tissue undergoing capsular ablation according to this invention, demonstrating extended monopolar mode applications with the embodiment shown in FIG. 10 to effect an encapsulated combined ablation and chemotherapy lesion. In this representation, the power applied has been pulsed to effect a cause a larger overall ablation geometry, the individual ablation patterns having merged into a single elongated, larger envelope 98 for the treatment fluids.

Figure 13:
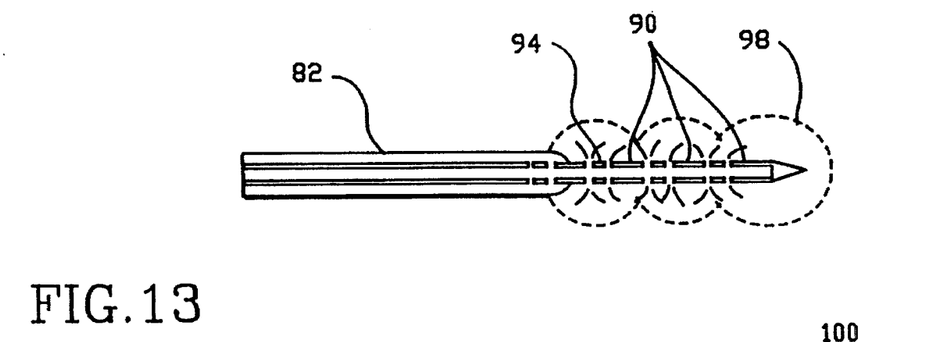
FIG. 13 is a schematic view of tissue undergoing capsular ablation according to this invention, demonstrating selection of bipolar modes with the embodiment shown in FIG. 10 to effect a desired ablation lesion geometry.

FIG. 13 is a schematic view of tissue undergoing capsular ablation according to this invention, demonstrating selection of bipolar modes with the embodiment shown in FIG. 10 to effect a desired ablation lesion geometry. The conductive sleeves 90 are connected to the power supply to effect current flow from each conductive sleeve to the conductive sleeves immediately adjacent thereto. This forms a spherical ablation diffusion barrier around each conductive path, overlapping with an adjacent sphere, and providing a roughly cylindrical ablation geometry and cylindrical infusion barrier capsule 100.

The device and method of this invention provides the physician with a flexible variety of ablation procedures, optionally combining application of ablation energy to elevate tissue temperature with the treatment zone to above 45° C. to cause death of cells therein, combined with fluid applications. Application of saline fluid can reduce desiccation of tissue adjacent the electrode surfaces.

Application of chemotherapeutic substances before application of the ablation energy can exploit the effects of the heating the tissue and the fluid to increase distribution of the fluid in the adjacent tissues. Application of chemotherapeutic substances after ablation forming an encapsulated lesion can reduce distribution of the chemotherapeutic agent to tissue beyond the ablation capsule, concentrating its activity to the tissues within the capsule and reducing and almost eliminating the systemic effects of the treatment. These alternatives and combinations thereof provide to a physician treating tissue containing neoplastic cells a wide range of alternatives. A treatment regimen can be devices combining any of these alternatives or all of them to increase the effectiveness of the treatment.

The ablation treatment according to this invention can be used in combination with systemic or localized chemotherapy.

Examples of chemotherapeutic agents suitable for use in the method of this invention include, but are not limited to anti-neoplastic agents. Suitable anti-neoplastic agents include, but are not limited to alkylating agents including alkyl sulfonates such as Busulfan, Improsulfan and Pipo- sulfan; aziridines such as Benzodepa, Carboquone, Meture- depa and Uredepa; ethylenimines and Methylmelamines such as Altretamine, Triethylenemelamine, Triethylenephosphoramide, Triethylenethiophosphoramide and Trimethylolmelamine; nitrogen mustards such as Chlorambucil, Chlornaphazine, Cyclophosphamide, Estramustine, Ifosfamide, Mechlorethamine, Mechlorethamine Oxide Hydrochloride, Melphalan, Novembichin, Phenesterine, Prednimustine, Trofosfamide and Uracil Mustard; nitrosoureas such as Carmustine, Chlorozotocin, Fotemustine, Lomustine, Nimustine, Ranimustine; and others such as Dacarbazine, Mannomustine, Mitrobronitol, Mitolactol and Pipobroman. Also included are antineoplastic antibiotics such as Aclacinomycines, Actinomycin, Anthramycin, Azaserine, Bleomycins, Cactinomycin, Carubicin, Carzinophilin, Chromomycins, Dactinomycin, Daunorubicin, 6-Diazo-5oxo-L-norleucine, Doxorubicin, Epirubicin, Mitomycins, Mycophenolic Acid, Nogalamycin, Olivomycins, Peplomycin, Plicamycin, Porfiromycin, Puromycin, Streptonigrin, Streptozocin, Tubercidin, Ubenimex, Zinostatin and Zorubicin. Also included are antineoplastic antimetabolites such as folic acid analogs such as Denopterin, Methotrexate, Pteropterin and Trimetrexate; purine analogs such as Fludarabine, 6-Mercaptopurine, Thiamiprine and Thioguanine; pyrimidine analogs such as Ancitabine, Azacitidine, 6-Azauridine, Carmofur, Cytarabine, Doxifluridine, Enocitabine, Floxuridine, Fluorouracil and Tegafur; enzymes such as L-Asparaginase; and others such as Aceglatone, Amsacrine, Bestrabucil, Bisantrene, Carboplatin, Cisplatin, Defosfamide, Demecolcine, Diaziquone, Eflornithine, Elliptinium Acetate, Etoglucid, Etoposide, Gallium Nitrate, Hydroxyurea, Interferon-α, Interfer-onβ, Interferon-γ, Interleukin-2, Lentinan, Lonidamine, Mitoguazone, Mitoxantrone, Mopidamol, Nitracrine, Pentostatin, Phenamet, Pirarubicin, Podophyllinic Acid; 2-Ethylhydrazide, Procarbazine, PSK, Razoxane, Sizofiran, Spirogermanium, Taxol, Teniposide, Tenuazonic Acid, Triaziquone, 2,2',2''-Trichlorotriethylamine, Urethan, Vinblasine, Vincristine and Vindesine.

This invention is shown by the following specific, but non-limiting examples.

EXAMPLE 1

RF Ablation Treatment of MXT Tumors

MXT tumors were implanted in 100 mice. MXT tumors were treated by RF ablation 17 days post-implantation and 30 days post-implantation. The MXT tumors show naturally intensive centro-acinar necrosis. The RF ablation power of 5, 6, and 9 watts was applied for 3, 5 and 7 minutes, and the most effective treatment was found to be with about 5.75 watts for 5 minutes.

The control group of mice was sacrificed at the same intervals as the treated group. The histological analysis follows:

1. Analysis of specimens at 0 hour post-treatment: No visible lesions

2. Analysis of specimens at 24 hours post-treatment: no lesion.

3. Analysis of specimens at 5 days post-treatment: apparition of necrotic lesions with dedifferentiation of basal acinar layer.

4. Analysis of specimens at 15 days post-treatment:

Macroscopically: Intensive and extensive necrosis. A sole peripheral crescent of viable tumor can be seen. It depends upon the ablation electrode deployment. The 1.5 and 3 cm tumors are equally affected as the electrode deployment is viable along the tumor size.

Microscopically: Deep and almost complete destruction of MXT tumors with ghosts of necrotic glandular acini. The normal necrosis of the MXT tumors is essentially centro-acinar. In comparison, the necrosis induced by the electrode RF ablation affects the entire acini that only remains as ghosts acini but with subsisting architecture.

At the nuclear level, even the macroscopically unaffected areas, transformation of ovoid tumor nuclei in polygonal nuclei were observed

EXAMPLE 2

Comparative Treatment of MXT Tumors with RF Ablation and/or Chemotherapy

This example shows a comparison of RF ablation, chemotherapy and a combination of RF ablation and chemotherapy in tumor area progression.

Mice were separated into four groups as follows:

1. Control—15 mice

2. Mice treated with RF ablation 17 day post-implantation—15 mice

3. Mice treated with 9 intraperitoneal chemotherapy injections of Etoposid, Cyclophosphamid and Adriablastine from day 17 post-implantation with implantation—15 mice.

4. Mice treated at day 17 with RF ablation and with 9 intraperitoneal chemotherapy injections from day 17 post-implantation with Etoposid, Cyclophosphamid and Adriablastine.

The tumor reductions differences achieved were statistically significant between evolution of control tumors and all other groups.

The most effective group was the association of chemotherapy and RF ablation with the device of this invention. The difference between RF ablation and chemotherapy was non-statistically concluant. The statistical difference between the RF ablation, alone, and the combination of chemotherapy and RF ablation favors the combination treatment.

The results shown in Examples 1 and 2 support the following conclusion: 1) RF ablation with the device of this invention is effective in decreasing tumor progression. 2) After an initial decrease at day 7 post-RF ablation treatment, tumors increase in size, indicating that a small viable tumor cell population is responsible for this increase. Two simultaneous RF ablation treatments on each side of the tumor is expected to improve the tumor reduction. 3) The RF ablation with the device of this invention enhances the chemotherapy treatment, and the combination of the chemotherapy and RF ablation produces a dramatic decrease in tumor size and a destruction of living tumor cells.

To those skilled in the art to which this invention relates, many changes in construction and widely differing embodiments and applications of the invention will make themselves know without departing from the spirit and scope of the invention. The disclosure and the description herein are purely illustrative and are not intended to be in any sense limiting.

We claim:

1. An RF ablation device for delivering chemotherapeutic agents to a tissue treatment site and for creating a diffusion barrier capsule to impede diffusion of chemotherapeutic agents from the tissue treatment site, the ablation device comprising:

a hollow tubular Rf electrode having a closed, sharpened distal tip and a conductive surface to which Rf power is supplied to heat the tissue treatment site to a temperature between about 45° C. and 170° C. to produce a diffusion barrier capsule, the Rf electrode also including a plurality of fluid distribution ports distributed along the length of the electrode for delivering chemotherapeutic agents to the tissue treatment site; and a fluid distribution port blocking implement positioned within the hollow tubular Rf electrode whose position within the electrode is adjustable to prevent fluid from passing through one or more of the plurality of fluid distribution ports.

2. An Rf ablation device according to claim 1 wherein the device further includes an insulating sleeve covering the electrode, the insulating sleeve being moveable along the length of the electrode to define an electrode conductive surface.

3. An Rf ablation device according to claim 1 wherein the electrode includes a plurality of conductive segments for delivering Rf energy, each conductive segment being insulated from neighboring segments and connected to a power delivery controller which controls the power delivered to each conductive segment.

4. An Rf ablation device according to claim 3 wherein the power delivery controller also controls the polarity of each conductive segment.

5. An Rf ablation device according to claim 3 wherein the device further includes an insulating sleeve covering the electrode, the insulating sleeve being moveable along the length of the electrode to define an electrode conductive surface.

6. An Rf ablation device according to claim 5 wherein the power delivery controller also controls the polarity of each conductive segment.

7. An Rf ablation device according to claim 1 wherein the tubular Rf electrode is composed of a shaped-memory metal.

8. An Rf ablation device according to claim 7 wherein the electrode further includes an insulating sleeve covering the electrode, the insulating sleeve being moveable along the length of the electrode to define an electrode conductive surface.

9. An Rf ablation device according to claim 7 wherein the electrode includes a plurality of conductive segments for delivering Rf energy, each conductive segment being insulated from neighboring conductive segments and connected to a power delivery controller which controls the power delivered to each conductive segment.

10. An Rf ablation device according to claim 9 wherein the power delivery controller also controls the polarity of each conductive segment.

11. A method for delivering chemotherapeutic agents to a tissue treatment site and for impeding diffusion of the chemotherapeutic agents from the tissue treatment site through the creation of a diffusion barrier capsule, the method comprising the steps of:

a) introducing an Rf ablation device into a tissue treatment site, the device including a hollow tubular Rf electrode having a closed, sharpened distal tip, an electrode conductive surface for conducting Rf ablation, and a plurality of fluid distribution ports distributed along the length of the electrode for delivering chemotherapeutic agents to the tissue treatment site;

b) supplying Rf power to the electrode to produce a diffusion barrier capsule at the tissue treatment site; and c) introducing chemotherapeutic agents to the tissue treatment site through at least one of the fluid distribution ports, the diffusion barrier capsule impeding the diffusion of the chemotherapeutic agents from the tissue treatment site.

12. The method according to claim 11 wherein the device further includes a fluid distribution port blocking implement positioned within the hollow tubular Rf electrode, further comprising the step of positioning the position of the blocking implement within the electrode being adjustable to prevent fluid from passing through one or more of the plurality of fluid distribution ports.

13. The method according to claim 11 further comprising the step of heating the body tissues to a temperature between about 80° C. and 170° C. to produce the diffusion barrier capsule.

14. The method according to claim 1 wherein the device further includes a moveable insulating sleeve covering the electrode, the method further comprising the step of positioning the insulating sleeve along the length of an electrode to define the electrode conductive surface.

15. The method according to claim 14 wherein the tubular Rf electrode is composed of a shaped-memory metal, the method further comprising the step of moving the insulating sleeve to expose a portion of the electrode wherein the portion of the electrode exposed reverts to its memory shape.

16. The method according to claim 1 further comprising the step of passing fluid through the fluid distribution ports while Rf energy is supplied to the electrode in order to reduce dehydration of tissue at the tissue treatment site during ablation.

17. A method for delivering chemotherapeutic agents to a tissue treatment site and for impeding diffusion of the chemotherapeutic agents from the tissue treatment site through the creation of a diffusion barrier capsule, the method comprising the steps of:

a) introducing an Rf ablation device into a tissue treatment site, the device including a hollow tubular Rf electrode having a closed, sharpened distal tip, an electrode conductive surface for conducting Rf ablation, and a plurality of fluid distribution ports distributed along the length of the electrode for delivering chemotherapeutic agents to the tissue treatment site, the device further including a fluid distribution port blocking implement positioned within the hollow tubular Rf electrode, the position of the blocking implement within the electrode being adjustable to prevent fluid from passing through one or more of the plurality of fluid distribution ports;

b) supplying Rf power to the electrode to produce a diffusion barrier capsule at the tissue treatment site;

c) adjusting the position of the blocking implement to prevent fluid from passing through one or more of the plurality of fluid distribution ports; and d) introducing chemotherapeutic agents to the tissue treatment site through at least one fluid distribution port, the diffusion barrier capsule impeding the diffusion of the chemotherapeutic agents from the tissue treatment site.

18. A method for delivering chemotherapeutic agents to a tissue treatment site and for impeding diffusion of the chemotherapeutic agents from the tissue treatment site through the creation of a diffusion barrier capsule, the method comprising the steps of:

a) introducing an Rf ablation device into a tissue treatment site, the device including a hollow tubular Rf electrode having a closed, sharpened distal tip, a plurality of fluid distribution ports distributed along the length of the electrode for delivering chemotherapeutic agents to the tissue treatment site, and a plurality of conductive segments for delivering Rf energy, each segment being insulated from neighboring segments and connected to a power delivery controller which controls the power delivered to each conductive segment;

b) selecting the power delivered to each conductive segment using the power delivery controller;

c) supplying Rf power to the electrode to produce a diffusion barrier capsule at the tissue treatment site; and d) introducing chemotherapeutic agents to the tissue treatment site through at least one fluid distribution port, the diffusion barrier capsule impeding the diffusion of the chemotherapeutic agents from the tissue treatment site.

19. A method according to claim 18 wherein the device further includes a fluid distribution port blocking implement positioned within the hollow tubular Rf electrode, the position of the blocking implement within the electrode being adjustable to prevent fluid from passing through one or more ports of the plurality of fluid distribution ports, the method comprising the further step of:

adjusting the position of the blocking implement within the hollow tubular Rf electrode to prevent fluid from passing through one or more ports of the plurality of fluid distribution ports.

* * * * *